(12) United States Patent
Marsh et al.

(10) Patent No.: US 10,568,820 B2
(45) Date of Patent: Feb. 25, 2020

(54) METHOD OF INHIBITING COPPER DEPOSITION ON HAIR

(71) Applicant: Noxell Corporation, Hunt Valley, MD (US)

(72) Inventors: Jennifer Mary Marsh, Deerfield Township, OH (US); Graham Neil McKelvey, Hampshire (GB)

(73) Assignee: Noxell Corporation, Hunt Valley, MD (US)

( * ) Notice: Subject to any disclaimer, the term of this patent is extended or adjusted under 35 U.S.C. 154(b) by 0 days.

(21) Appl. No.: 14/971,385

(22) Filed: Dec. 16, 2015

(65) Prior Publication Data

US 2016/0175210 A1 Jun. 23, 2016

Related U.S. Application Data

(60) Provisional application No. 62/093,201, filed on Dec. 17, 2014.

(51) Int. Cl.
| | | |
|---|---|---|
| *A61Q 5/12* | (2006.01) | |
| *A61K 8/362* | (2006.01) | |
| *A61K 8/02* | (2006.01) | |
| *A61K 8/04* | (2006.01) | |
| *A61K 8/22* | (2006.01) | |
| *A61K 8/34* | (2006.01) | |
| *A61K 8/36* | (2006.01) | |
| *A61K 8/37* | (2006.01) | |
| *A61K 8/42* | (2006.01) | |
| *A61K 8/46* | (2006.01) | |
| *A61K 8/49* | (2006.01) | |
| *A61K 8/55* | (2006.01) | |
| *A61K 8/891* | (2006.01) | |
| *A61K 8/898* | (2006.01) | |
| *A61Q 5/02* | (2006.01) | |
| *A61Q 5/06* | (2006.01) | |

(52) U.S. Cl.
CPC ............ *A61K 8/362* (2013.01); *A61K 8/0216* (2013.01); *A61K 8/042* (2013.01); *A61K 8/22* (2013.01); *A61K 8/342* (2013.01); *A61K 8/361* (2013.01); *A61K 8/37* (2013.01); *A61K 8/375* (2013.01); *A61K 8/42* (2013.01); *A61K 8/463* (2013.01); *A61K 8/4946* (2013.01); *A61K 8/55* (2013.01); *A61K 8/891* (2013.01); *A61K 8/898* (2013.01); *A61Q 5/02* (2013.01); *A61Q 5/065* (2013.01); *A61Q 5/12* (2013.01)

(58) Field of Classification Search
None
See application file for complete search history.

(56) References Cited

U.S. PATENT DOCUMENTS

| | | | |
|---|---|---|---|
| 6,365,143 B1 | 4/2002 | Lundmark et al. | |
| 6,451,300 B1* | 9/2002 | Dunlop | A61K 8/0254 424/70.1 |
| 7,179,302 B2* | 2/2007 | Boswell | A61K 8/44 132/202 |
| 7,186,275 B2* | 3/2007 | Boswell | A61K 8/44 132/202 |
| 7,300,647 B1* | 11/2007 | O'Toole | A61K 8/44 424/401 |
| 2006/0078528 A1* | 4/2006 | Yang | A61K 8/342 424/70.27 |
| 2009/0246236 A1* | 10/2009 | Kitko | A61K 8/342 424/401 |
| 2013/0174863 A1 | 7/2013 | Marsh et al. | |
| 2013/0333715 A1* | 12/2013 | Hutton, III | A61K 8/88 132/202 |
| 2014/0335036 A1* | 11/2014 | Marsh | A61K 8/4946 424/62 |

FOREIGN PATENT DOCUMENTS

| | | |
|---|---|---|
| CN | 107106441 A | 8/2017 |
| EP | 1370223 B1 | 12/2010 |
| EP | 2937112 A1 | 10/2015 |
| JP | 2004524333 A | 8/2004 |
| WO | 93/08787 A2 | 5/1993 |
| WO | 97/24106 A1 | 7/1997 |
| WO | 97/24108 A1 | 7/1997 |
| WO | 98/04237 A1 | 2/1998 |
| WO | 2014/182766 A1 | 11/2014 |

(Continued)

OTHER PUBLICATIONS

"International Application Serial No. PCT/US2015/064717, International Search Report dated Feb. 29, 2016", 3 pgs.
"International Application Serial No. PCT/US2015/064717, Written Opinion dated Feb. 29, 2016", 6 pgs.
"International Application Serial No. PCT/US2015/064717, International Preliminary Report on Patentability dated Jun. 29, 2017", 8 pgs.
"Japanese Application Serial No. 2017-533292, Office Action dated Aug. 14, 2018", w/ English translation, 6 pgs.

(Continued)

*Primary Examiner* — Tigabu Kassa
(74) *Attorney, Agent, or Firm* — Schwegman Lundberg & Woessner, P.A.

(57) ABSTRACT

A method of inhibiting copper deposition on hair and facilitating the removal of copper deposited on hair including applying to the hair a bleaching or oxidative dyeing composition comprising a chelant, rinsing the bleaching or oxidative dyeing composition, applying to the hair a rinse-off conditioner composition comprising histidine, rinsing the rinse-off conditioner composition from the hair, applying to the hair a shampoo composition having ethylenediamine-N,N'-disuccinic acid and/or histidine, rinsing the shampoo composition from the hair, applying to the hair a rinse-off conditioner composition comprising histidine, and rinsing the conditioner composition from the hair.

19 Claims, 1 Drawing Sheet

(56) References Cited

FOREIGN PATENT DOCUMENTS

WO    WO-2016100036 A1    6/2016
WO    WO-2016100036 A9    6/2016

OTHER PUBLICATIONS

"Japanese Application Serial No. 2017-533292, Examiners Decision of Final Refusal dated Jan. 29, 2019", 5 pgs.
"Japanese Application Serial No. 2017-533292, Response filed Nov. 13, 2018 to Office Action dated Aug. 14, 2018", w/ English Claims, 16 pgs.
"Japanese Application Serial No. 2017-533292, Response filed May 29, 2019 to Examiners Decision of Final Refusal dated Jan. 29, 2019", w/ English Claims, 64 pgs.
PCT International search Report and Written Opinion dated Feb. 29, 2016.
"Brazilian Application Serial No. BR112017012739-3, Office Action dated Aug. 27, 2019", w/ English Translation, 5 pgs.

* cited by examiner

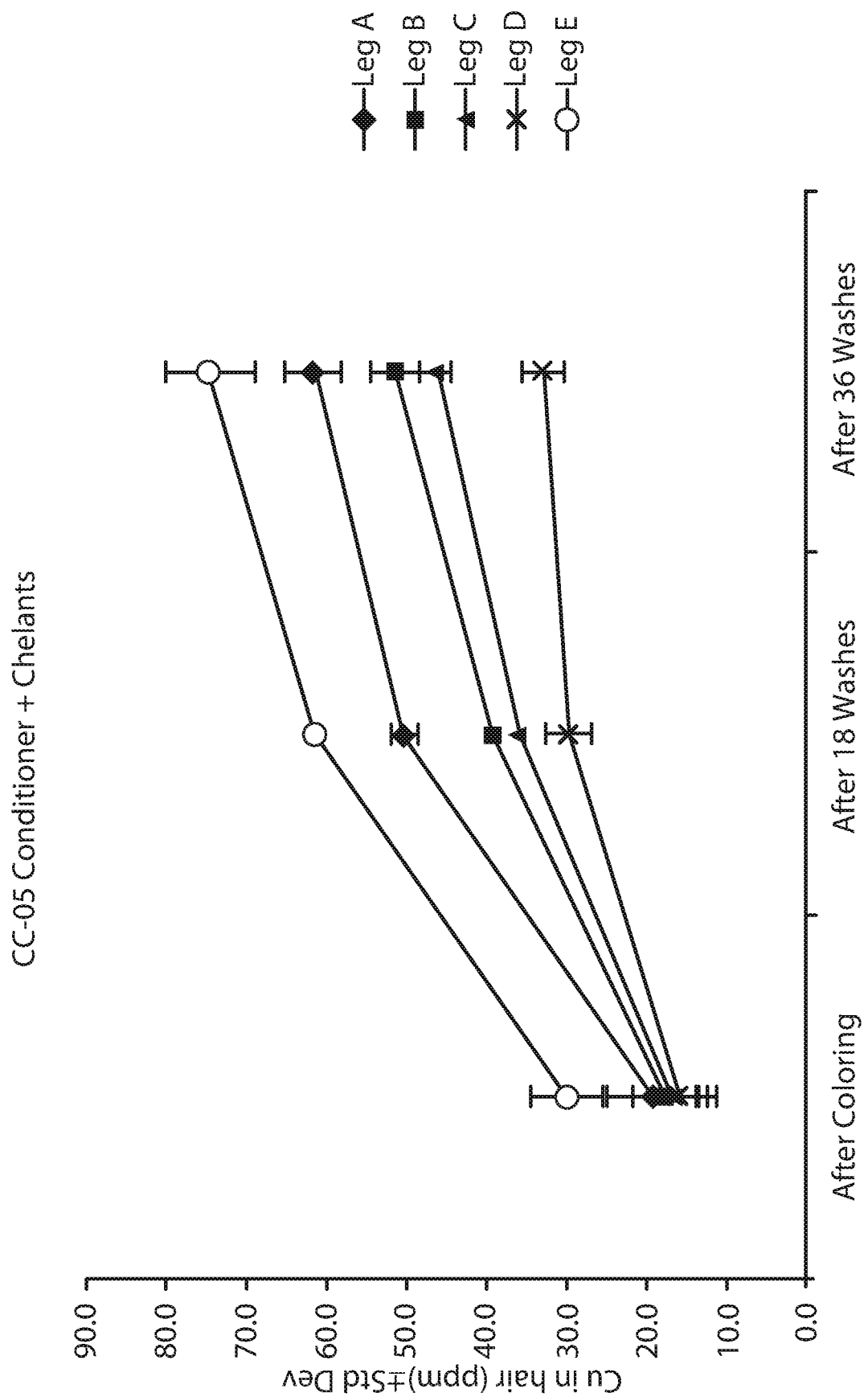

METHOD OF INHIBITING COPPER DEPOSITION ON HAIR

FIELD OF THE INVENTION

The present invention relates to a method of inhibiting copper deposition on hair and facilitating the removal of copper deposited on hair.

BACKGROUND OF THE INVENTION

Many water sources that are used by consumers for personal care contain elevated levels of calcium and magnesium salts, as well as undesirable levels of redox metals salts. As such, using chelants to sequester trace redox metals often proves to be ineffective because most chelants also competitively bind calcium and/or magnesium.

It has been found that even trace quantities of copper can deposit on the hair surface and in between the cuticle layers of hair. This deposition of copper on hair is especially problematic because transition metal ions, such as copper and iron, can facilitate reduction-oxidation (redox) reactions during hair coloring treatments and during UV exposure. These reactions generate reactive oxygen species (ROS), which in turn can cause damage to the hair. In addition, they can interfere with the oxidative color formation chemistry and lead to reduced color uptake for hair colorant users.

Accordingly, there is a need for an improved hair care regimen that can inhibit copper deposition on hair, as well as facilitate the removal of copper already deposited thereon.

Consumers use a variety of hair care products for their personal hygiene and improved appearance. Shampoo products are routinely used daily (or less frequently) by many consumers to clean their hair. Shampoos contain detersive surfactants that remove sebum, dirt and other residues from hair after water rinsing. Many of these consumers apply rinse-off hair conditioners in a separate step after shampoo washing to achieve better combability, hair damage repair, hair damage protection, hair feel and appearance. Hair conditioners typically contain silicones, organic oils, cationic surfactants or other hydrophobic conditioning agents that are deposited on hair surfaces and provide these benefits. Other consumers also use leave-on-treatments, after the application and rinsing of the shampoo and the rinse-off conditioners, for additional or more effective conditioning benefits.

Hair bleaching and colorant products are also commonly used today to provide a better hair appearance. Most specifically, hair bleaching compositions contain oxidizing agents in an alkali solution. They are used to oxidize the natural hair melanin and their use results in lighter colored hair.

Oxidizing agents are also used during oxidative dyeing treatments, which represent the most commonly used hair colorants. Coloring consumers typically dye their hair using such products every 6-8 weeks.

Application of permanent dyeing or bleaching compositions result in some hair fiber damage, making consumers' hair more hydrophilic, difficult to comb, more porous and feeling less soft than undamaged hair. For that reason, these compositions are typically sold as a kit along with a rinse-off conditioner. This rinse-off conditioner is applied on the hair after the bleaching or dyeing composition has been rinsed off. Typically, such "in-box" conditioners contain higher concentration of silicone or other conditioning agents and result in more effective hair conditioning than the typical routine conditioners that consumers use after their routine shampoo. Some consumers use such "in-box" conditioners more frequently than their 6-8 weeks hair coloring for more effective hair conditioning. A possible frequency of using "in-box" rinse-off conditioner is every 1-2 weeks. It was surprisingly found that the use of combinations of hair care products that contain varying types and levels of chelants is able to remove copper salts from hair significantly more effectively, providing protection from hair damage caused by UV and contributing to hair health, in particular when an oxidative hair dye is used.

SUMMARY OF THE INVENTION

A method of inhibiting copper deposition on hair and facilitating the removal of copper deposited on hair includes the steps of applying to the hair a bleaching or oxidative dyeing composition comprising a chelating agent, rinsing the bleaching or oxidative dyeing composition, applying to the hair a conditioner composition comprising histidine, rinsing the conditioner composition from the hair, applying to the hair a shampoo composition having ethylenediamine-N,N'-disuccinic acid (EDDS) and/or histidine, rinsing the shampoo composition from the hair, applying to the hair a rinse-off conditioner composition comprising histidine, and rinsing the conditioner composition from the hair. Optionally, additional leave-on treatments containing chelating agents can be applied to the hair. This method can be repeated 1 or more times.

BRIEF DESCRIPTION OF THE DRAWINGS

FIG. 1 is a graph indicating test results.

DETAILED DESCRIPTION OF THE INVENTION

While the specification concludes with claims particularly pointing out and distinctly claiming the invention, it is believed that the present invention will be better understood from the following description.

As used herein, the term "fluid" includes liquids and gels.

As used herein, the term "log x" refers to the common (or decadic) logarithm of x.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "M.Wt." refers to the weight average molecular weight unless otherwise stated.

As used herein, the terms "include," "includes," and "including," are meant to be non-limiting and are understood to mean "comprise," "comprises," and "comprising," respectively.

All percentages, parts and ratios are based upon the total weight of the compositions of the present invention, unless otherwise specified. All such weights as they pertain to listed ingredients are based on the active level and, therefore; do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Copper Reduction Regimens

The objective of the regimen is to minimize the level of copper in hair to as low a level as possible. It is believed that copper, that may come from tap water, in the presence of an oxidative event such as an oxidative colorant or UV exposure, will accelerate formation of reactive oxygen species (ROS). These ROS will react with the structural proteins and lipids of hair leading over time to breakage and loss of shine, manageability etc. The role of copper in accelerating the formation of these ROS is catalytic so even low levels will have the potential to cause significant damage.

It is advantageous to add chelants to each component of the regimen as each exposure to water, e.g. rinsing after shampoo or conditioning steps, may introduce copper back into hair. However, the choice of chelants for each product form and which step to include in the regimen may impact performance. It has been found unexpectedly that different components in the regimen have different chelation efficiency (when used in the particular hair product) and thus the combination of the components gives the lowest final copper level in hair.

For the colorant the factor to consider when selecting a chelant is its ability to prevent the one electron radical formation chemistry of copper in the presence of high levels of an oxidant; typically hydrogen peroxide at pH 10. The chelant can also be specific to binding copper in the presence of high levels of calcium (present in hair typically at 100× higher levels). Delivery of chelant to copper is not as important a factor as product dosage levels are comparatively high (~4 g product per g of hair).

EDDS is an effective chelant in a colorant as it can efficiently prevent the one electron chemistry of copper in the presence of hydrogen peroxide by its ability to form a stable hexadentate Cu-EDDS-Cu complex. It also has a high relative binding constant for Cu vs Ca. Histidine which binds copper in a bidentate arrangement does not as efficiently prevent one electron chemistry of copper, and ROS are still formed.

For the shampoo, conditioner and leave-on treatments (LOTs) the objective is to efficiently remove copper from hair so when the hair is exposed to UV oxidation between coloring damage is minimized. For the shampoo and leave-on treatments EDDS is also the chelant of choice due to its high Ca/Cu specificity. For the conditioning compositions histidine is the chelant of choice as it can be readily formulated into the conditioner gel network structure. EDDS is typically not readily incorporated into many conditioner formulations except at very low levels due in part to its high negative charge. In addition from this product form, histidine will more readily penetrate hair and remove copper from inside hair.

Surprisingly it was found that a daily use of shampoo and conditioner ("first conditioning composition") in combination with the weekly after-color, often provided as an in-box conditioner ("second conditioning composition") regimen is the most efficient way to minimize copper levels in hair. Inclusion of a weekly treatment on top of daily use improved copper removal efficiency by over 50% from the rinse-off steps even though only 24% more chelant was added with its inclusion in the regimen.

EDDS & Histidine

Histidine and ethylenediamine-N,N'-disuccinic acid (EDDS) are both chelants. It has been found that histidine and EDDS compounds have the high Formation Constant $K_{ML}$ for copper and the low Formation Constant for calcium that is desired for efficient inhibition of deposition of copper (see Table 1 below) and can be formulated up to a level of 0.25% in shampoos. Histidine and/or EDDS may be present in a hair care composition such as a colorant composition, a shampoo composition, a rinse-off conditioner composition, and/or leave-on treatment at a level of from about 0.025% to about 0.25%, alternatively from about 0.05% to about 0.2%, and alternatively from about 0.1% to about 0.15%, by weight of the hair care composition, conditioner composition, or leave-on treatment.

The Formation Constant of a metal chelant interaction is defined as:

$$K_{ML} = \frac{[ML]}{[M][L]}$$

where:
[ML]=concentration of metal ligand complex at equilibrium
[M]=concentration of free metal ion
[L]=concentration of free ligand in a fully deprotonated form
$K_{ML}$=formation constant for the metal chelant complex. All concentrations are expressed in mol/dm$^3$. Formation Constants are conveniently expressed as logarithms.

TABLE 1

| Amino Acid | Log $K_{ML}$ Cu | Log $K_{ML}$ Ca |
|---|---|---|
| Histidine | 10.2 | 1.2 |
| Asparagine | 7.8 | — |
| Tryptophan | 8.2 | — |
| Serine | 7.9 | 1.4 |
| Glutamine | 7.7 | — |
| Alanine | 8.1 | 1.3 |
| Glycine | 8.2 | 1.1 |
| Proline | 8.8 | — |
| EDDS | 18.4 | 4.6 |

The hair care compositions described herein may comprise ethylenediamine-N,N'-disuccinic acid (EDDS), derivatives, and/or salts thereof at levels sufficient to deliver adequate copper removal performance and to reduce copper uptake into hair. EDDS compounds for use herein may be in the free acid form, and salts thereof. Salts may include alkali metal, alkaline earth metals, ammonium or substituted ammonium salts. In an embodiment, the salts include sodium, potassium, magnesium, or calcium salts. Examples of sodium salts of EDDS include Na$_2$EDDS and Na$_3$EDDS. The structure of the acid form of EDDS is as follows:

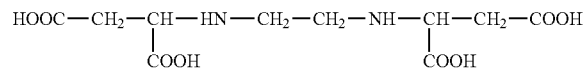

EDDS may be synthesized, for example, from readily available, inexpensive starting materials such as maleic anhydride and ethylenediamine. The synthesis of EDDS from maleic anhydride and ethylene diamine may yield a mixture of three optical isomers, [R,R], [S,S], and [S,R] (25% S,S, 50% R,S and 25% R,R), due to the two asymmetric carbon atoms. The biodegradation of EDDS may be optical isomer-specific, with the [S,S] isomer degrading most rapidly and extensively.

The hair care compositions described herein comprises histidine. Histidine compounds means compounds according to the general formula (I) below wherein each X is independently selected from substituted or unsubstituted, saturated or unsaturated carbon, preferably unsubstituted and saturated carbon.

n is 0-10, preferably 0-2, more preferably 0

R1 is selected from hydrogen, alkyl, aryl, arylalkyl or alkaryl, preferably hydrogen or alkyl, more preferably hydrogen Y is a heteroatom, preferably nitrogen Q is selected from nil, hydrogen, aryl or alkyl, preferably hydrogen R3 is selected from hydrogen, alkyl, aryl, arylalkyl or alkaryl, preferably hydrogen or alkyl, more preferably hydrogen R4 is independently selected from hydrogen and alkyl, preferably hydrogen

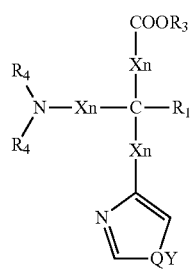

Suitable histidine compounds for use herein include histidine and ester derivatives of histidine. Histidine compounds contain a chiral center and are present in the D- and L-form. For present compositions either form is acceptable as is a mixture of the D- and L-forms.

A person skilled in the art could manufacture histidine compounds using standard techniques. See, for example, *Organic Chemistry, Fifth Edition*, T W Graham Soloman, John Wiley & Son Inc (1992) 1092-1136.

A suitable method of inhibiting copper deposition on hair and facilitating the removal of copper deposited on hair comprising the steps of
(a) applying to the hair a hair colorant composition selected from the group consisting of bleaching compositions and an oxidative dyeing compositions comprising EDDS;
(b) rinsing said hair colorant composition from the hair with water;
(c) applying to the hair a first conditioner composition comprising:
  (1) from about 0.025% to about 0.25% histidine, by weight of the conditioner composition;
  (2) a conditioner gel matrix comprising
    (i) from 0.1% to about 20% of one or more high melting point fatty compound, by weight of the conditioner gel matrix;
    (ii) from about 0.1% to about 10% of a cationic surfactant system, by weight of the conditioner gel matrix; and
    (iii) at least 20% of a second aqueous carrier, by weight of the conditioner gel matrix;
  (3) from about 1% to about 8% of a silicone;
(d) rinsing said conditioner first composition from the hair with water;
(e) applying to the hair a shampoo composition comprising
  (1) from about 0.025% to about 0.25% of a compound selected from the group consisting of ethylenediamine-N,N'-disuccinic acid, derivatives of ethylenediamine-N,N'-disuccinic acid, salts of ethylenediamine-N,N'-disuccinic acid, salts of derivatives of ethylenediamine-N,N'-disuccinic acid, histidine and mixtures thereof, by weight of the shampoo composition; and
  (2) from about 2% to about 50% of one or more detersive surfactants, by weight of the shampoo composition;
(f) rinsing said shampoo composition from the hair with water;
(g) applying to the hair a second conditioner composition comprising
  (1) from about 0.025% to about 0.25% histidine, by weight of the second conditioner composition;
  (2) a conditioner gel matrix comprising
    (i) from 0.1% to about 20% of one or more high melting point fatty compound, by weight of the conditioner gel matrix;
    (ii) from about 0.1% to about 10% of a cationic surfactant system, by weight of the conditioner gel matrix; and
    (iii) at least 20% of a second aqueous carrier, by weight of the conditioner gel matrix;
(h) rinsing said second conditioner composition from the hair with water;
wherein steps (e), (f), (g), (h) are repeated one or more times until the desirable hair copper content is achieved.

The bleaching or the oxidative dyeing composition may also comprise from about 0.025% to about 0.25% of a compound selected from the group consisting of ethylenediamine-N,N'-disuccinic acid (EDDS), derivatives of ethylenediamine-N,N'-disuccinic acid, salts of ethylenediamine-N,N'-disuccinic acid, salts of derivatives of ethylenediamine-N,N'-disuccinic acid, histidine and mixtures thereof, by weight of the colorant composition.

The second conditioner composition used in step (c) may also comprise from about 2% to about 8% silicone by weight of the second conditioner composition. The second conditioner composition may comprise from about 4% to about 6% silicone by weight of the second conditioner composition. The silicone may be selected from the group consisting of a amodimethicone, a silicone resin, a dimethicone, a dimethiconol, and/or a mixture thereof. The second conditioner can be provided along with the dyeing composition as an in box conditioner.

Steps (e), (f) (g) and (h) can be repeated every 1 to 7 days. Alternatively, every about 5 to about 10 repetitions of these steps, the second conditioner composition used comprises (1) from about 0.025% to about 0.25% histidine, by weight of the conditioner composition; (2) a conditioner gel matrix comprising (i) from 0.1% to about 20% of one or more high melting point fatty compound, by weight of the conditioner gel matrix; (ii) from about 0.1% to about 10% of a cationic surfactant system, by weight of the conditioner gel matrix; and (iii) at least 20% of a second aqueous carrier, by weight of the conditioner gel matrix; and (3) from about 2% to about 8% silicone by weight of the conditioner composition. Alternatively, the second conditioner composition comprises from about 4% to about 6% silicone by weight of the conditioner composition. The silicone may be selected from the group consisting of an amodimethicone, a silicone resin, a dimethicone, a dimethiconol, and/or a mixture thereof. Optionally, a leave-on-treatment composition may be applied on the hair after the rinsing step following the second conditioner application step. The application of a leave-on-treatment may be performed after every rinsing step following the second conditioner application step or, in the case of repeated cycles of step (e), (f) and (g) steps, only occasionally. The composition of the leave-on-treatment may comprise from about 0.025% to about 0.25% of a compound selected from the group consisting of ethylenediamine-N,N'-disuccinic acid (EDDS), derivatives of ethylenediamine-N,N'-disuccinic acid, salts of ethylenediamine-N,N'-disuccinic acid, salts of derivatives of ethylenediamine-N,N'-disuccinic acid, histidine and mixtures thereof, by weight of said leave-on-treatment composition Hair Bleaching or Oxidative Dyeing Composition The method of inhibiting copper deposition on hair and facilitating the removal of copper deposited on hair described herein comprises applying to the hair a bleaching or oxidative dyeing composition. The hair bleaching composition delivers consumer desired hair lightening shampooing in addition to inhibiting the deposition of copper (i.e. from the water used to rinse) on the hair.

A hair bleaching or oxidative dyeing composition may comprise from about 0.025% to about 0.25%, alternatively from about 0.05% to about 0.2%, alternatively from about 0.1% to about 0.15% of a compound selected from the group consisting of ethylenediamine-N,N'-disuccinic acid (EDDS), derivatives of ethylenediamine-N,N'-disuccinic acid (EDDS), salts of ethylenediamine-N,N'-disuccinic acid (EDDS), salts of derivatives of ethylenediamine-N,N'-disuccinic acid (EDDS), histidine, and mixtures thereof, by weight of the hair bleaching or oxidative dyeing composition.

As used herein, the term "oxidizing composition" means a composition comprising at least one oxidizing agent suitable for use on hair, such as hydrogen peroxide, sodium, potassium, ammonium or other salts of perborate, percarbonate, persulfate and percarbamide. Examples of such compositions are oxidative dye compositions and bleaching compositions.

The compositions according to the present invention compose or are used in combination with a composition that comprises at least one oxidizing agent. Suitable oxidizing agents for use herein are water-soluble peroxygen oxidizing agents. "Water-soluble" as defined herein means that in standard conditions at least about 0.1 g, and/or greater than about 1 g, and/or greater than about 10 g of said oxidizing agent can be dissolved in 1 liter of deionized water. The oxidizing agents are valuable for the initial solubilisation and decolorisation of the melanin (bleaching) and accelerate the polymerization of the oxidative dye precursors (oxidative dyeing) in the hair shaft.

Suitable water-soluble oxidizing agents are inorganic peroxygen materials capable of yielding hydrogen peroxide in an aqueous solution. Water-soluble peroxygen oxidizing agents are known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Mixtures of two or more such oxidizing agents can be used if desired. Suitable for use in the compositions according to the present invention is hydrogen peroxide.

In conventional dyeing and bleaching compositions, levels of peroxygen oxidizing agent are usually of from about 0.1% to about 7% by weight. Higher levels, while giving good results in term of efficacy were until now not practical because of increased hair damage. The oxidative damage protection provided by the composition makes it now possible to use oxidizing agent such as hydrogen peroxide in level up to 40% in the oxidizing composition. However, for safety reasons, levels above 12% should be investigated before being used on humans. In one embodiment the level of the oxidizing agent in the oxidizing composition is of from about 0.5% to about 20% by weight, and/or from about 1% to about 15%. The compositions according to the present invention provide excellent gray coverage, vibrant colors and acceptable damage at level above about 7% (typically about 12%).

The compositions of the present invention may be complex compositions, which in addition to the chelant and oxidizing agent comprise other components that may or may not be active ingredients. This includes, but is not limited to, buffering agents, hair dyeing agents such as oxidative dye precursors, non-oxidative dyes, thickeners, solvents, enzymes, anionic, nonionic, amphoteric and cationic surfactants, conditioning agents, carriers, antioxidants, stabilizers, perming actives, perfume, hair swelling agents and/or polymers.

The compositions may be substantially free from organic peroxyacid precursors and preformed organic peroxyacid, such as those defined in WO97/24106. These include sodium nonanoylbenzenesulfonate (NOBS), acetyltriethylcitrate (ATC), sodium (6-nonaamidocaproyl)oxybenzenesulfonate, peracetic and pernanoic acid and can have a negative effect on the efficiency of bleaching and coloring and increase damage at a pH above 8. The term substantially free as used herein means that the compositions according to the present invention should comprise less than 1.5%, less than 1%, less than 0.5% and/or less than 0.1% by weight of the composition of such compounds.

Finally, the compositions can be provided in any usual form, such as for example an aqueous composition, a powder, a gel or an oil-in-water emulsion.

A. pH Buffering Agents

The compositions according to the present invention can further comprise a pH buffering agent. The pH of the composition is preferably of from about 8 to about 12, from about 9 to about 11, and/or from about 9.5 to about 10.5. Suitable buffering agents are well known in the art and include for example ammonia/ammonium acetate mixture and monoethanolamine (MEA).

B. Oxidative Hair Dye Precursors

These compounds are well known in the art, and include aromatic diamines, aminophenols and their derivatives (a representative but not exhaustive list of oxidation dye precursor can be found in Sagarin, "Cosmetic Science and Technology", "Interscience, Special Edn. Vol. 2 pages 308 to 310). Precursors can be used with couplers. Couplers are generally colorless molecules that can form colors in the presence of activated precursors.

The choice of precursors and couplers will be determined by the color, shade and intensity of coloration that is desired. The precursors and couplers can be used herein, singly or in combination, to provide dyes having a variety of shades ranging from ash blonde to black.

Hair dye compositions will generally comprise from about 0.001% to about 10%, and/or from about 0.1% to about 2%, of oxidative dye precursors and couplers.

C. Thickeners

The composition of the present invention may optionally further comprise at least about 0.1% of thickeners. Thickeners are comprised in amount sufficient to provide the composition with a viscosity of from about 1 Pa·s to 10 Pa·s (about 1,000 to about 10,000 cP) at 26 deg.C. in order to provide a composition that can be readily applied to the hair without dripping.

Suitable for use herein are salt tolerant thickeners. A non exclusive list of suitable salt tolerant thickeners for use herein include xanthan, guar, hydroxypropyl guar, scleroglucan, methyl cellulose, ethyl cellulose (commercially available as Aquacote (Registered trademark), hydroxyethyl cellulose (Natrosol (Registered trademark), carboxymethyl cellulose, hydroxypropylmethyl cellulose, microcrystalline cellulose, hydroxybutylmethyl cellulose, hydroxypropyl cellulose (Klucel (Registered trademark), hydroxyethyl ethyl cellulose, cetyl hydroxyethyl cellulose (Natrosol (Registered trademark Plus 330), N-vinylpyrollidone (Povidone (Registered trademark), Acrylates/Ceteth-20 Itaconate Copolymer (Structure (Registered trademark 3001), hydroxypropyl starch phosphate (Structure (Registered trademark ZEA), polyethoxylated urethanes or polycarbamyl polyglycol ester (e.g. PEG-150/Decyl/SMDI copolymer=Aculyn (Registered trademark 44, PEG-150/Stearyl/SMDI copolymer=Aculyn 46 (Registered trademark), trihydroxystearin (Thixcin (Registered trademark) acrylates copolymer (e.g. Aculyn (Registered trademark 33) or hydrophobically modified acrylate copolymers (e.g. Acrylates/Steareth-20 Methacrylate Copolymer=Aculyn (Registered trademark 22).

Fatty alcohols have thickening properties and can be used in the compositions of present invention. Fatty alcohols are however not salt-tolerant thickeners according to the above definition. A mixture of 2% cetyl and stearyl alcohol has for example a viscosity of less than about 0.7 Pa·s (700 cP) as measured at 26 deg.C. with a Brookfield viscometer in the conditions disclosed hereabove.

Shampoo Composition

The method of inhibiting copper deposition on hair and facilitating the removal of copper deposited on hair described herein comprises applying to the hair a shampoo composition. The shampoo composition delivers consumer desired shampooing in addition to inhibiting the deposition of copper (i.e. from the water used to rinse) on the hair.

The shampoo composition comprises from about 0.025% to about 0.25%, alternatively from about 0.05% to about 0.2%, alternatively from about 0.1% to about 0.15% of a compound selected from the group consisting of ethylenediamine-N,N'-disuccinic acid (EDDS), derivatives of ethylenediamine-N,N'-disuccinic acid (EDDS), salts of ethylenediamine-N,N'-disuccinic acid (EDDS), histidine, and mixtures thereof, by weight of the shampoo composition. After applying to the hair a shampoo composition as described herein, the method then comprises rinsing the shampoo composition from the hair.

A. Detersive Surfactant

It has been found that chelants possessing a stronger affinity for redox metals (e.g., transition metal ions such as $Cu^{+2}$ and/or $Fe^{+3}$) over that of alkaline-earth metal ions such as $Ca^{+2}$ at pH about 2 to about 6 efficiently inhibit the deposition of redox metals on keratinous, and can reduce the amount of redox metal salt deposits already existing on the keratinous tissue. The typical chelants that have high affinity for transition metal ions are typically negatively charged and contain polycarboxylate ions such as EDDS (ethylenediamine disuccinic acid) and EDTA (ethylenediamine tetraacetic acid) or polyphosphonic ions such as diethylenetriamine-penta-(methylenephosphonic acid) (DTPMP). It has been surprisingly found that histidine compounds also possesses strong affinity for copper over that of calcium and magnesium and that they are unique amongst the amino acids.

The shampoo composition may comprise one or more detersive surfactants, which provides cleaning performance to the composition. The one or more detersive surfactants in turn may comprise an anionic surfactant, amphoteric or zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the shampoo composition should be sufficient to provide the desired cleaning and lather performance, and generally ranges from about 2 wt % to about 50 wt %, from about 5 wt % to about 30 wt %, from about 8 wt % to about 25 wt %, from about 10 wt % to about 20 wt %, about 5 wt %, about 10 wt %, about 12 wt %, about 15 wt %, about 17 wt %, about 18 wt %, or about 20 wt %.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment, the anionic surfactant is sodium lauryl sulfate or sodium laureth sulfate.

Suitable amphoteric or zwitterionic surfactants for use in the shampoo composition herein include those which are known for use in shampoo or other personal care cleansing. Concentrations of such amphoteric surfactants range from about 0.5 wt % to about 20 wt %, and from about 1 wt % to about 10 wt %. Non limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the shampoo composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present shampoo composition include cocoamphoacetate, cocoamphodiacetate, lauroamphoacetate, lauroamphodiacetate, and mixtures thereof.

Zwitterionic detersive surfactants suitable for use in the shampoo composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non limiting examples of other anionic, zwitterionic, amphoteric or optional additional surfactants suitable for use in the shampoo composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

The shampoo composition may also comprise a shampoo gel matrix, an aqueous carrier, and other additional ingredients described herein.

B. Aqueous Carrier

The shampoo composition comprises a first aqueous carrier. Accordingly, the formulations of the shampoo composition can be in the form of pourable liquids (under ambient conditions). Such compositions will therefore typically comprise a first aqueous carrier, which is present at a level of at least 20 wt %, from about 20 wt % to about 95 wt %, or from about 60 wt % to about 85 wt %. The first aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The first aqueous carriers useful in the shampoo composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

C. Shampoo Gel Matrix

The shampoo composition described herein may comprise a shampoo gel matrix. The shampoo gel matrix comprises (i) from about 0.1% to about 20% of one or more fatty alcohols, alternative from about 0.5% to about 14%, alternatively from about 1% to about 10%, alternatively from about 6% to about 8%, by weight of the shampoo gel matrix; (ii) from about 0.1% to about 10% of one or more shampoo gel matrix surfactants, by weight of the shampoo gel matrix; and (iii) from about 20% to about 95% of an aqueous carrier, alternatively from about 60% to about 85% by weight of the shampoo gel matrix.

The fatty alcohols useful herein are those having from about 10 to about 40 carbon atoms, from about 12 to about 22 carbon atoms, from about 16 to about 22 carbon atoms, or about 16 to about 18 carbon atoms. These fatty alcohols can be straight or branched chain alcohols and can be saturated or unsaturated. Nonlimiting examples of fatty alcohols include, cetyl alcohol, stearyl alcohol, behenyl alcohol, and mixtures thereof. Mixtures of cetyl and stearyl alcohol in a ratio of from about 20:80 to about 80:20 are suitable.

The shampoo gel matrix surfactants may be any of the detersive surfactants described in section "A" herein.

The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carrier useful herein includes water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

Conditioner Composition

The method of inhibiting copper deposition on hair and facilitating the removal of copper deposited on hair described herein comprises applying to the hair a conditioner composition after rinsing the shampoo composition from the hair. The conditioner composition described herein delivers consumer desired conditioning in addition to inhibiting the deposition of copper (i.e. from the water used to rinse) on the hair.

The conditioner composition described herein comprises (i) from about 0.025% to about 0.25%, alternatively from about 0.05% to about 0.2%, alternatively from about 0.1% to about 0.15% histidine, by weight of the conditioner composition, and (ii) a conditioner gel matrix. After applying to the hair a conditioner composition as described herein, the method then comprises rinsing the conditioner composition from the hair. The conditioner composition also comprises a conditioner gel matrix comprising (1) one or more high melting point fatty compounds, (2) a cationic surfactant system, and (3) a second aqueous carrier.

A. Cationic Surfactant System

The conditioner gel matrix of the conditioner composition includes a cationic surfactant system. The cationic surfactant system can be one cationic surfactant or a mixture of two or more cationic surfactants. The cationic surfactant system can be selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt, a combination of mono-long alkyl amindoamine salt and mono-long alkyl quaternized ammonium salt.

The cationic surfactant system can be included in the composition at a level by weight of from about 0.1% to about 10%, from about 0.5% to about 8%, from about 0.8% to about 5%, and from about 1.0% to about 4%.

Mono-Long Alkyl Quaternized Ammonium Salt

The monoalkyl quaternized ammonium salt cationic surfactants useful herein are those having one long alkyl chain which has about 22 carbon atoms and in one embodiment a C22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

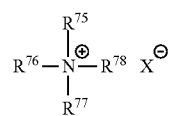

(I)

wherein one of $R^{75}$, $R^{76}$, $R^{77}$ and $R^{78}$ is selected from an alkyl group of 22 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 22 carbons, or higher, can be saturated or unsaturated. One of $R^{75}$, $R^{76}$, $R^{77}$ and $R^{78}$ can be selected from an alkyl group of about 22 carbon atoms, the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt.

Mono-Long Alkyl Amidoamine Salt

Mono-long alkyl amines are also suitable as cationic surfactants. Primary, secondary, and tertiary fatty amines are useful. Particularly useful are tertiary amido amines having an alkyl group of about 22 carbons. Exemplary tertiary amido amines include: behenamidopropyldimethylamine, behenamidopropyldiethylamine, behenamidoethyldiethylamine, behenamidoethyldimethylamin. Useful amines in the present invention are disclosed in U.S. Pat. No. 4,275,055, Nachtigal, et al. These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; in one embodiment l-glutamic acid, lactic acid, and/or citric acid. The amines herein can be partially neutralized with any of the acids at a molar ratio of the amine to the acid of from about 1:0.3 to about 1:2, and/or from about 1:0.4 to about 1:1.

Di-Long Alkyl Quaternized Ammonium Salt

Di-long alkyl quaternized ammonium salt can be combined with a mono-long alkyl quaternized ammonium salt or mono-long alkyl amidoamine salt. It is believed that such combination can provide easy-to-rinse feel, compared to single use of a monoalkyl quaternized ammonium salt or mono-long alkyl amidoamine salt. In such combination with a mono-long alkyl quaternized ammonium salt or mono-long alkyl amidoamine salt, the di-long alkyl quaternized ammonium salts are used at a level such that the wt % of the dialkyl quaternized ammonium salt in the cationic surfactant system is in the range of from about 10% to about 50%, and/or from about 30% to about 45%.

The di-long alkyl quaternized ammonium salt cationic surfactants useful herein are those having two long alkyl chains having about 22 carbon atoms. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Di-long alkyl quaternized ammonium salts useful herein are those having the formula (II):

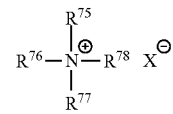

(II)

wherein two of $R^{75}$, $R^{76}$, $R^{77}$ and $R^{78}$ is selected from an alkyl group of from 22 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 22 carbons, or higher, can be saturated or unsaturated. One of $R^{75}$, $R^{76}$, $R^{77}$ and $R^{78}$ can be selected from an alkyl group of from 22 carbon atoms, the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Such dialkyl quaternized ammonium salt cationic surfactants include, for example, dialkyl (C22) dimethyl ammonium chloride, ditallow alkyl dimethyl ammonium chloride, dihydrogenated tallow alkyl dimethyl ammonium chloride. Such dialkyl quaternized ammonium salt cationic surfactants also include, for example, asymmetric dialkyl quaternized ammonium salt cationic surfactants.

B. High Melting Point Fatty Compound

The conditioner gel matrix of the conditioner composition includes one or more high melting point fatty compounds. The high melting point fatty compounds useful herein may have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are suitable for use in the conditioner composition. The fatty alcohols useful herein are those having from about 14 to about 30 carbon atoms, from about 16 to about 22 carbon atoms. These fatty alcohols are saturated and can be straight or branched chain alcohols. Suitable fatty alcohols include, for example, cetyl alcohol, stearyl alcohol, behenyl alcohol, and mixtures thereof.

High melting point fatty compounds of a single compound of high purity can be used. Single compounds of pure fatty alcohols selected from the group of pure cetyl alcohol, stearyl alcohol, and behenyl alcohol can also be used. By "pure" herein, what is meant is that the compound has a purity of at least about 90%, and/or at least about 95%. These single compounds of high purity provide good rinsability from the hair when the consumer rinses off the composition.

The high melting point fatty compound can be included in the conditioner composition at a level of from about 0.1% to about 20%, alternatively from about 1% to about 15%, and alternatively from about 1.5% to about 8% by weight of the composition, in view of providing improved conditioning benefits such as slippery feel during the application to wet hair, softness and moisturized feel on dry hair.

C. Aqueous Carrier

The conditioner gel matrix of the conditioner composition includes a second aqueous carrier. Accordingly, the formulations of the conditioner composition can be in the form of pourable liquids (under ambient conditions). Such compositions will therefore typically comprise a second aqueous carrier, which is present at a level of from about 20 wt % to about 95 wt %, or from about 60 wt % to about 85 wt %. The second aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The second aqueous carriers useful in the conditioner composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Leave-On Treatment

The method of inhibiting copper deposition on hair and facilitating the removal of copper deposited on hair described herein may also comprise applying a leave-on treatment to the hair after rinsing the conditioner from the hair. The leave-on treatment described herein may deliver consumer desired conditioning in addition to inhibiting the deposition of copper (i.e. from the water used to rinse) on the hair.

The leave-on treatment described herein may comprise from about 0.025% to about 0.25%, alternatively from about 0.05% to about 0.2%, alternatively from about 0.1% to about 0.15% of a compound selected from the group consisting of ethylenediamine-N,N'-disuccinic acid (EDDS), derivatives of ethylenediamine-N,N'-disuccinic acid (EDDS), salts of ethylenediamine-N,N'-disuccinic acid (EDDS), and mixtures thereof, by weight of the leave-on treatment. The leave-on treatment also comprises (1) one or more rheology modifiers and (2) a third aqueous carrier.

A. Rheology Modifier

In one embodiment the leave-on treatment may include one or more rheology modifiers to adjust the rheological characteristics of the composition for better feel, in-use properties and the suspending stability of the composition. For example, the rheological properties are adjusted so that the composition remains uniform during its storage and transportation and it does not drip undesirably onto other areas of the body, clothing or home furnishings during its use. Any suitable rheology modifier can be used. In an embodiment, the leave-on treatment may comprise from about 0.01% to about 3% of a rheology modifier, alternatively from about 0.1% to about 1% of a rheology modifier, The one or more rheology modifier may be selected from the group consisting of polyacrylamide thickeners, cationically modified polysaccharides, associative thickeners, and mixtures thereof. Associative thickeners include a variety of material classes such as, for example: hydrophobically modified cellulose derivatives; hydrophobically modified alkoxylated urethane polymers, such as PEG-150/decyl alcohol/SMDI copolymer, PEG-150/stearyl alcohol/SMDI copolymer, polyurethane-39; hydrophobically modified, alkali swellable emulsions, such as hydrophobically modified polypolyacrylates, hydrophobically modified polyacrylic acids, and hydrophobically modified polyacrylamides; hydrophobically modified polyethers. These materials may have a hydrophobe that can be selected from cetyl, stearyl, oleayl, and combinations thereof, and a hydrophilic portion of repeating ethylene oxide groups with repeat units from 10-300, alternatively from 30-200, and alternatively from 40-150. Examples of this class include PEG-120-methylglucose dioleate, PEG-(40 or 60) sorbitan tetraoleate, PEG-150 pentaerythrityl tetrastearate, PEG-55 propylene glycol oleate, PEG-150 distearate.

Non-limiting examples of additional rheology modifiers include acrylamide/ammonium acrylate copolymer (and) polyisobutene (and) polysorbate 20; acrylamide/sodium acryloyldimethyl taurate copolymer/isohexadecane/polysorbate 80; acrylates copolymer; acrylates/beheneth-25 methacrylate copolymer; acrylates/C10-C30 alkyl acrylate crosspolymer; acrylates/steareth-20 itaconate copolymer; ammonium polyacrylate/Isohexadecane/PEG-40 castor oil; C12-16 alkyl PEG-2 hydroxypropylhydroxyethyl ethylcellulose (HM-EHEC); carbomer; crosslinked polyvinylpyrrolidone (PVP); dibenzylidene sorbitol; hydroxyethyl ethylcellulose (EHEC); hydroxypropyl methylcellulose (HPMC); hydroxypropyl methylcellulose (HPMC); hydroxypropylcellulose (HPC); methylcellulose (MC); methylhydroxyethyl cellulose (MEHEC); PEG-150/decyl alcohol/SMDI copolymer; PEG-150/stearyl alcohol/SMDI copolymer; polyacrylamide/C13-14 isoparaffin/laureth-7; polyacrylate 13/polyisobutene/polysorbate 20; polyacrylate crosspolymer-6; polyamide-3; polyquaternium-37 (and) hydrogenated polydecene (and) trideceth-6; polyurethane-39; sodium acrylate/acryloyldimethyltaurate/dimethylacrylamide; crosspolymer (and) isohexadecane (and) polysorbate 60; sodium polyacrylate. Exemplary commercially-available rheology modifiers include ACULYN™ 28, Klucel M CS, Klucel H CS, Klucel G CS, SYLVACLEAR AF1900V, SYLVACLEAR PA1200V, Benecel E10M, Benecel K35M, Optasense RMC70, ACULYN™33, ACULYN™46, ACULYN™22, ACULYN™44, Carbopol Ultrez 20, Carbopol Ultrez 21, Carbopol Ultrez 10, Carbopol 1342, Sepigel™ 305, Simulgel™600, Sepimax Zen, and/or combinations thereof.

B. Aqueous Carrier

The leave-on treatment may comprise a third aqueous carrier. Accordingly, the formulations of the leave-on treatment can be in the form of pourable liquids (under ambient conditions). Such compositions will therefore typically comprise a third aqueous carrier, which is present at a level of at least 20 wt %, from about 20 wt % to about 95 wt %, or from about 60 wt % to about 85 wt %. The third aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The third aqueous carriers useful in the leave-on treatment include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

pH

The shampoo composition, rinse-off first and second conditioner composition, and/or leave-on treatment may have a pH in the range from about 2 to about 10, at 25° C. In an embodiment, the shampoo composition, rinse-off conditioner composition, and/or leave-on treatment may have a pH in the range of from about 2 to about 6, alternatively from about 3.5 to about 5, alternatively from about 5.25 to about 7, which may help to solubilize copper and redox metals already deposited on the hair. Thus, the shampoo composition, rinse-off conditioner composition, and/or leave-on treatment can also be effective toward washing out the existing copper and redox metals deposits, which can reduce cuticle distortion and thereby reduce cuticle chipping and damage. In an embodiment, the shampoo composition and/or rinse-off conditioner composition may comprise citric acid, wherein the citric acid acts as a buffer.

Additional Components

The shampoo composition, conditioner compositions, and/or leave-on treatments described herein may optionally comprise one or more additional components known for use in hair care or personal care products, provided that the additional components are physically and chemically compatible with the essential components described herein, or do not otherwise unduly impair product stability, aesthetics or performance. Such additional components are most typically those described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the hair care compositions.

Non-limiting examples of additional components for use in the hair care compositions include conditioning agents, natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, proteins, skin active agents, sunscreens, UV absorbers, and vitamins.

1. Conditioning Agent

The hair care compositions may comprise one or more conditioning agents. Conditioning agents include materials that are used to give a particular conditioning benefit to hair. The conditioning agents useful in the hair care compositions of the present invention typically comprise a water-insoluble, water-dispersible, non-volatile, liquid that forms emulsified, liquid particles. Suitable conditioning agents for use in the hair care composition are those conditioning agents characterized generally as silicones, organic conditioning oils or combinations thereof, or those conditioning agents which otherwise form liquid, dispersed particles in the aqueous surfactant matrix.

One or more conditioning agents are present from about 0.01 wt % to about 10 wt %, from about 0.1 wt % to about 8 wt %, and from about 0.2 wt % to about 4 wt %, by weight of the composition.

Silicone Conditioning Agent

The compositions of the present invention may contain one or more silicone conditioning agents. Examples of the silicones include dimethicones, dimethiconols, cyclic silicones, methylphenyl polysiloxane, and modified silicones with various functional groups such as amino groups, quaternary ammonium salt groups, aliphatic groups, alcohol groups, carboxylic acid groups, ether groups, epoxy groups, sugar or polysaccharide groups, fluorine-modified alkyl groups, alkoxy groups, or combinations of such groups. Such silicones may be soluble or insoluble in the aqueous (or non-aqueous) product carrier. In the case of insoluble liquid silicones, the polymer can be in an emulsified form with droplet size of about 10 nm to about 30 micrometers Organic Conditioning Materials The conditioning agent of the compositions of the present invention may also comprise at least one organic conditioning material such as oil or wax, either alone or in combination with other conditioning agents, such as the silicones described above. The organic material can be nonpolymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-20 200, PEG-400, PEG-600, PEG-1000, PEG-2M, PEG-7M, PEG-14M, PEG-45M and mixtures thereof.

Benefit Agents

In an embodiment, the hair care composition further comprises one or more additional benefit agents. The benefit agents comprise a material selected from the group consisting of anti-dandruff agents, anti-fungal agents, anti-itch agents, anti-bacterial agents, anti-microbial agents, moisturization agents, anti-oxidants, vitamins, lipid soluble vitamins, perfumes, brighteners, enzymes, sensates, attractants, dyes, pigments, bleaches, and mixtures thereof.

The hair care compositions of the present invention may be presented in typical hair care formulations. They may be in the form of solutions, dispersion, emulsions, powders, talcs, encapsulated, spheres, spongers, solid dosage forms, foams, and other delivery mechanisms. The compositions of the embodiments of the present invention may be hair tonics, leave-on hair products such as treatment, and styling products, rinse-off hair products such as shampoos, and treatment products; and any other form that may be applied to hair.

According to one embodiment, the hair care compositions may be provided in the form of a porous, dissolvable solid structure, such as those disclosed in U.S. Patent Application Publication Nos. 2009/0232873; and 2010/0179083, which are incorporated herein by reference in their entirety. Accordingly, the hair care compositions comprise a chelant, a buffer system comprising an organic acid, from about 23% to about 75% surfactant; from about 10% to about 50% water soluble polymer; and optionally, from about 1% to about 15% plasticizer; such that the hair care composition is in the form of a flexible porous dissolvable solid structure, wherein said structure has a Percent open cell content of from about 80% to about 100%.

According to another embodiment, the hair care compositions may be in the form of a porous dissolvable solid structure comprising a chelant; a buffer system comprising an organic acid from about 23% to about 75% surfactant; wherein said surfactant has an average ethoxylate/alkyl ratio of from about 0.001 to about 0.45; from about 10% to about 50% water soluble polymer; and from about 1% to about 15% plasticizer; and wherein said article has a density of from about 0.03 g/cm$^3$ to about 0.20 g/cm$^3$.

According to another embodiment, the hair care compositions may be in the form of a viscous liquid comprising a chelant; a buffer system comprising an organic acid from 5-20% surfactant and a polycarboxylate rheology modifier; wherein the polycarboxylate is specifically chosen to be effective at the high electrolyte levels resulting from the incorporation of the key buffer system and chelant used for this invention. Non-limiting examples include acrylates/C10-C30 alkyl acrylate crosspolymers such as Carbopol EDT2020, 1342, 1382, etc. from Lubrizol. Rheology benefits of these actives in our embodiments include stability, ease of dispensing, smoothness of spreading, etc.

The hair care compositions are generally prepared by conventional methods such as are known in the art of making the compositions. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. The hair care composition may be in a single phase or a single product, or the hair care composition may be in a separate phases or separate products. If two products are used, the products may be used together, at the same time or sequentially. Sequential use may occur in a short period of time, such as immediately after the use of one product, or it may occur over a period of hours or days.

EXAMPLES

The following examples illustrate embodiments of the invention described herein. The exemplified oxidative dyeing, rinse-off conditioner, and shampoo compositions can be prepared by conventional formulation and mixing techniques. It will be appreciated that other modifications of the oxidative dyeing compositions, rinse-off conditioner compositions, and shampoo compositions within the skill of those in the formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

The following are non-limiting examples of oxidative dyeing compositions, shampoo compositions, and rinse-off conditioner compositions described herein.

Oxidative Dyeing Compositions Examples

Hair Colorant Example 1

Developer Formulation

| Ingredients | % Wt |
| --- | --- |
| Water | QS to 100% |
| Hydrogen Peroxide 50% solution | 17.80 |
| Etidronic acid 60% solution | 0.080 |
| Acrylates Copolymer 28% in water[1] | 7.83 |
| Steareth-21 | 2.00 |
| Acrylates steareth-20 methacrylate copolymer[2] | 1.70 |
| Conditioning oils | 4.00 |

[1]Aculyn 33A
[2]Aculyn 22

Dye Precursor Component Formulation

| Ingredients | Wt % |
| --- | --- |
| Water | 49.26 |
| Oleic acid | 2.00 |
| Cocoamidopropyl betaine high pH | 3.30 |
| Perfume | 1.20 |
| Trisodium EDDS | 3.02 |
| Citric acid | 0.40 |
| Isopropyl alcohol | 5.00 |
| Ammonium Hydroxide (25% NH3) | 7.20 |
| Sodium sulfite | 0.10 |
| Disodium EDTA | 0.05 |
| Erythrorbic acid | 0.40 |
| Oxidative dye precursors | 1.50 |
| Oleth-5 | 3.00 |
| Oleth-2 | 1.50 |
| C12-15 Pareth-3 | 0.50 |
| C12-15 Pareth-9 | 1.00 |
| Cosolvent (Ethoxydiglycol & Propylene glycol) | 20.00 |
| EDDS | 0.50 |

Example 2: Hair Dye Cream

Dye Precursor Composition

| Ingredients | % Wt |
| --- | --- |
| Cetylstearylalcohol | 15.00 |
| Glyceryl monostearate | 2.30 |
| Lanolin | 0.80 |
| Lanolin alcohol | 3.80 |
| Sodium lauryl diglykolether sulfate (28% aqueous solution) | 3.50 |
| Steareth-20 | 1.42 |
| Ethanol | 7.80 |
| Ascorbic acid | 0.30 |
| Ethylenediaminetetraacetic acid disodium salt hydrate | 0.30 |
| Trisodium Ethylenediamine disuccinate | 0.125 |
| Ammonium hydroxide (22% aqueous solution) | 10.00 |
| Perfume | 0.20 |
| Dye precursors (appropriate mixture) | 1.00 |
| Demineralized water | QS to 100% |

The pH of the cream is between 9.5 and 10.5.

Immediately prior to application 75 g of the above-described dye carrier mass B are mixed with 50 grams of a 9% by weight aqueous hydrogen peroxide solution. The resulting ready-to-use hair dye mixture is applied to the hair in the specified amount. After an acting time of 30 minutes at 40° C. the hair is washed with a shampoo, rinsed with water and dried.

Example 3: Nonionic Hair Dye

Dye Precursor Composition

| Ingredients | % Wt |
| --- | --- |
| Cetylstearyl alcohol | 7.00 |
| Glyceryl oleate | 2.00 |
| Polysorbate 40 | 13.00 |
| Ceteareth-50 | 6.00 |
| Sodium sulfite, anhydrous | 0.50 |
| Ethylenediaminetetraacetic acid disodium salt | 0.10 |
| Trisodium Ethylenediamine disuccinate | 0.20 |
| Ammonia (25% aqueous solution) | 8.00 |
| Dye precursors (appropriate mixture) | 1.00 |
| Demineralized water | QS to 100% |

Hydrogen Peroxide Emulsion

| Ingredients | % Wt |
| --- | --- |
| Cetylstearyl alcohol | 3.00 |
| PEG-25 cetyl/stearyl ether | 0.80 |
| Lanolin alcohol | 0.30 |
| Hydrogen peroxide | 6.00 |
| Phosphoric acid (85% strength aqueous solution) | 0.10 |
| Demineralized water | QS to 100% |

60 g of the above non-ionic dye carrier mass E is mixed prior to application with 60 g of the above hydrogen peroxide emulsion (pH=2.5). The pH of the resulting ready-to-use hair dye composition is about 10. The resulting ready-to-use hair dye mixture is applied to bleached hair in the specified amount. After an acting time of 30 minutes at 40° C. the hair is washed with a shampoo, rinsed with water and dried.

Example 4: Hair Dye

Dye Precursor Composition

| Ingredients | % Wt |
| --- | --- |
| Sodium sulphite | 0.100 g |
| Ascorbic Acid | 0.200 g |
| Ethylenediaminetetraacetic acid disodium salt | 0.003 g |
| Citric Acid | 0.200 g |
| Ammonia (30% strength aqueous solution) | 4.000 g |
| Acrylates Copolymer (Aculyn ® 33A) | 1.000 g |
| Oleth 5 | 0.500 g |
| Oleth 2 | 1.000 g |
| Oleic Acid | 0.900 g |
| Cocamidopropyl betaine | 3.000 g |
| Etidronic Acid | 0.05 g |
| Trisodium Ethylenediamine disuccinate | 1.000 g |
| Isopropyl alcohol | 2.500 g |
| Hydrogen Peroxide (35% aqueous solution) | 8.600 g |
| Soytrimonium Chloride and propylene glycol | 3.000 g |
| Simethicone | 0.003 g |
| Steareth-21 | 1.000 g |
| PEG-50 Hydrogenated Palmamide | 0.500 g |
| Oleyl Alcohol | 0.200 g |
| Acrylates Steareth-20 Methacrylate Copolymer (Aculyn ® 22) | 0.500 g |
| Propylene Glycol | 2.000 g |
| Ethoxy Diglycol | 4.200 g |
| C11-15 Pareth-9 | 0.500 g |
| C12-15 Pareth-3 | 0.800 g |
| Dye precursors (appropriate mixture) | 1.000 g |
| Demineralized water | QS to 100% |

The pH of the ready-to-use hair dye composition is about 10. The ready-to-use hair dye mixture is applied to bleached hair in the specified amount. After an acting time of 40 minutes at 30° C. the hair is washed with a shampoo, rinsed with water and dried.

In-Box Rinse-Off Conditioner Composition Examples

| Ingredients | In-Box Conditioner Example 1 Wt % | In-Box Conditioner Example 2 Wt % | In-Box Conditioner Example 3 Wt % |
| --- | --- | --- | --- |
| Water | QS to 100% | QS to 100% | QS to 100% |
| L-Glutamic acid[1] | 0.64 | 0.64 | 0.64 |
| Stearamidopropyl dimethylamine[1] | 2.0 | 2.0 | 2.0 |
| Cetyl Alcohol | 4.5 | 4.5 | 4.5 |
| Stearyl Alcohol | 2.5 | 2.5 | 2.5 |
| EDTA | 0.10 | 0.10 | 0.10 |

-continued

| Ingredients | In-Box Conditioner Example 1 Wt % | In-Box Conditioner Example 2 Wt % | In-Box Conditioner Example 3 Wt % |
|---|---|---|---|
| Benzyl alcohols | 0.40 | 0.40 | 0.40 |
| Methylchloroisothiazolinone/ methylisothiazolinone | 0.033 | 0.033 | 0.033 |
| Amodimethicone[3] | 5.0 | 5.0 | 5.0 |
| Trimethylsiloxysilicate MQ Resin | 0.005 | 0.005 | 0.005 |
| Panthenyl ether ether | 0.225 | 0.225 | 0.225 |
| D,L-Panthenol | 0.045 | 0.045 | 0.045 |
| Perfume | 0.40 | 0.40 | 0.40 |
| Histidine | 0 | 0.10 | 0.25 |

[1]Supplied by Ajinomoto Ltd
[2]Supplied by Inolex under trade name Lexamine S-13
[3]Supplied by Wacker under the name ADM1100

Shampoo Composition Examples

| Ingredients | Shampoo Example 1 wt % | Shampoo Example 2 wt % |
|---|---|---|
| Water Purified | Q.S to 100 | Q.S to 100 |
| Sodium Laureth 3 Sulfate 28% solution | 21.6 | 21.6 |
| Sodium Lauryl Sulfate 29% solution | 34.5 | 34.5 |
| Laureth-4 | 0.9 | 0.9 |
| Dimethicone 330M cps | 0.5 | 0.5 |
| Glycol Distearate | 1.5 | 1.5 |
| Polyquaternium-6 | 0.32 | 0.32 |
| Trisodium ethylenediamine disuccinate | 0 | 0.10 |
| Sodium Benzoate | 0.27 | 0.27 |
| Citric acid 50% Solution | 0.52 | 0.52 |
| Methylchloroisothiazolinone/ methylisothiazolinone | 0.035 | 0.035 |
| Sodium chloride | 1.66 | 1.66 |
| Fragrance | 0.65 | 0.65 |
| DL-Panthenol 56% solution | 0.05 | 0.05 |
| Panthenyl Ethyl ether | 0.03 | 0.03 |
| Trisodium ethylenediamine disuccinate | 0.27 | 0.27 |
| Glycol Distearate | 1.5 | 1.5 |

Additional Shampoo Examples

| Ingredient | SH Ex 3 | SH Ex 4 | SH Ex 5 | SH Ex 6 | SH Ex 7 | SH Ex 8 | SH Ex 9 |
|---|---|---|---|---|---|---|---|
| Sodium lauryl ether sulfate (SLE3S) | | 6 | 10 | 6 | 6 | 9 | |
| Sodium cocoyl isethionate | | | | | | | 8.5 |
| sodium lauryl sulfate (SLS) | 1.5 | 7 | 1.5 | 7 | 7 | 6 | |
| sodium lauryl ether sulfate (SLE1S) | 10.5 | | | | | | |
| Disodium laureth sulfosuccinate | | | | | | | 8.5 |
| Sodium lauryl sulfoacetate | | | | | | | 2.5 |
| Sodium Lauroyl Sarcosinate | | | | | | | 0.75 |
| Cocoamidopropyl Hydroxysultaine | | | | | | | 1.5 |
| Cocoamidopropyl Betaine | 1 | 2 | 2 | 2 | 2 | 2 | 2 |
| Coconut monoethanol amide (CMEA) | | 0.85 | | 0.85 | | | |
| Cetyl alcohol | | | | 1 | | | |
| Stearyl alcohol | | | | 2 | | | |
| Dimethicone | 1 | 1 | 1 | 1 | 1 | | 0.5 |
| Ethylene glycol distearate (EGDS) | 1.5 | 1.5 | 1.5 | 1.5 | 1.5 | | |
| Jaguar ® C500[1] | 0.25 | 0.25 | 0.15 | | | | |
| Synthetic Cationic Polymer AMT[2] | | | | 0.1 | | | |
| Polydiallyldimethylammonium chloride (DADMAC) | | | | | 0.1 | | |
| Excel Guar[3] | | | | | | 0.1 | .15 |
| Ethylene diamine disuccinic acid (EDDS) | 0.1 | | 0.1 | | | 0.1 | |
| Histidine | | 0.1 | | 0.1 | 0.05 | | 0.1 |
| pH | 6 | 6 | 6 | 6 | 6 | 6 | |
| Water-USP Purified & Minors | Q.S. to 100 | Q.S. to 100 | Q.S. to 100 | Q.S. to 100 | Q.S. to 100 | Q.S. to 100 | Q.S. to 100 |

[1]Cationic polymer derived from a natural gum with low aqueous viscosity
[2]Cationic synthetic copolymer
[3]Cationic plant derived polymer

| Ingredient | SH Ex. 10 | SH Ex. 11 | SH Ex. 12 | SH Ex 13 |
|---|---|---|---|---|
| Water-USP Purified & Minors | Q.S. to 100 | Q.S. to 100 | Q.S. to 100 | Q.S. to 100 |
| Sodium Laureth Sulfate (SLE1S) | 12 | 14 | 12 | 14 |

| Ingredient | SH Ex. 10 | SH Ex. 11 | SH Ex. 12 | SH Ex 13 |
|---|---|---|---|---|
| Sodium Lauryl Sulfate (SLS) | 1.5 | | 1.5 | |
| Cocoamidoproply Betaine (CapB) | 1.7 | 1.7 | 1.7 | 1.7 |
| Gel Network | 1.0 | 1.0 | 2.0 | 2.0 |
| Guar Hydroxypropyltrimonium Chloride | 0.3 | 0.3 | 0.3 | 0.3 |
| Polyquaternium 6 (DADMAC) | 0.1 | 0.1 | 0.1 | 0.1 |
| Ethylene Glycol Distearate | 1.5 | | 1.5 | |
| Trihydroxy Stearin (Thixcin) | | 0.1 | | 0.1 |
| Dimethicone/Dimethiconol | 1.0 | 1.0 | 0.5 | 0.5 |
| Citric Acid | 1.0 | 1.0 | 1.0 | 1.0 |
| Sodium Citrate Dihydrate | 1.0 | 1.0 | 1.0 | 1.0 |
| Acrylates/C10-C30 alkyl acrylate crosspolymers | | 0.3 | | |
| Histidine | 0.05 | 0.1 | 0.05 | 0.1 |
| Kathon | 0.0005 | 0.0005 | 0.0005 | 0.0005 |
| Sodium Benzoate | 0.25 | 0.25 | 0.25 | 0.25 |
| Disodium EDTA | 0.1274 | 0.1274 | 0.1274 | 0.1274 |
| Perfume | 0.8 | 0.8 | 0.8 | 0.8 |
| Sodium Chloride[1] | 0-3 | 0-3 | 0-3 | 0-3 |
| Sodium Xylene Sulfonate[1] | 0-3 | 0-3 | 0-3 | 0-3 |

[1] Levels adjusted to reach desired viscosity

Shampoo Gel Matrix Method of Preparation

The shampoo gel matrix may be formed by combining fatty alcohols and surfactants in the ratio of 1:1 to 40:1, alternatively from 2:1 to 20:1, and alternatively from 3:1 to 10:1. The formation of a shampoo gel matrix involves heating a dispersion of the fatty alcohol in water with the surfactant to a temperature above the melting point of the fatty alcohol. During the mixing process, the fatty alcohol melts, allowing the surfactant to partition into the fatty alcohol droplets. The surfactant brings water along with it into the fatty alcohol. This changes the isotropic fatty alcohol drops into liquid crystalline phase drops. When the mixture is cooled below the chain melt temperature, the liquid crystal phase is converted into a solid crystalline gel matrix.

Example Shampoo Gel Matrix Composition

| Ingredient | Wt. % |
|---|---|
| Water | Qs |
| Cetyl Alcohol | 4% |
| Steary Alcohol | 8% |
| Sodium laureth-1 sulfate (28% Active) | 11% |

Rinse-Off Conditioner Formulations

| Ingredients | Rinse-off Conditioner Ex 1 Wt % | Rinse-off Conditioner Ex 2 Wt % |
|---|---|---|
| Amodimethicone 10000 cps | 0.50 | 0.50 |
| Citric acid anhydrous | 0.13 | 0.13 |
| DL-Panthenol 56% solution | 0.054 | 0.054 |
| Panthenyl Ethyl ether | 0.03 | 0.03 |
| Perfume | 0.50 | 0.50 |
| Hydroxypropyl guar (Jaguar HP-105) | 0.350 | 0.350 |
| Quaternium-18 | 0.750 | 0.750 |
| Steramidopropyldimethylamine | 1.00 | 1.00 |
| Gryceryl stearate | 0.25 | 0.25 |
| Cetearyl alcohol and Polysorbate 60 Emulsion [1] | 0.50 | 0.50 |
| Cetyl alcohol | 1.20 | 1.20 |
| Stearyl alcohol | 0.80 | 0.80 |
| Benzyl alcohol | 0.40 | 0.40 |
| Methylchloroisothiazolinone/methylisothiazolinone | 0.033 | 0.033 |
| Histidine | 0 | 0.05 |
| Water Purified | QS to 100 | QS to 100 |

[1] Lipowax P from Lipo (looked in internet)

Additional Examples of Rinse-Off Hair Conditioning Compositions

| Components | Rinse-off Condition Ex. 3 | Rinse-off Condition Ex. 4 | Rinse-off Condition Ex. 5 | Rinse-off Condition Ex. 6 | Rinse-off Condition Ex. 7 | Rinse-off Condition Ex. 8 |
|---|---|---|---|---|---|---|
| Water-USP Purified & Minors | QS to 100% | QS to 100% | QS to 100% | QS to 100% | QS to 100% | QS to 100% |
| BTMS[1] | 2.3 | 2.3 | 2.3 | 2.3 | 2.3 | 2.3 |
| BTMAC[2] | — | — | — | — | — | — |
| Cetyl alcohol | 1.1 | 1.1 | 1.1 | 1.1 | 1.1 | 1.1 |

-continued

| Ingredients | | | | | | |
|---|---|---|---|---|---|---|
| Stearyl alcohol | 2.8 | 2.8 | 2.8 | 2.8 | 2.8 | 2.8 |
| Soy Oligomer[3] | 1.0 | — | — | — | — | — |
| Soy Oligomer Blend[4] | — | 1.0 | — | — | — | — |
| Aminosilicone[5] | 1.0 | 1.0 | 1.0 | 1.0 | 2.0 | 2.0 |
| Perfume | 0.5 | 0.5 | 0.5 | 0.5 | 0.5 | 0.5 |
| Disodium EDTA | 0.1 | 0.1 | 0.1 | 0.1 | 0.1 | 0.1 |
| Panthenol | 0.03 | 0.03 | 0.03 | 0.03 | 0.03 | 0.03 |
| Panthenyl ethyl ether | 0.03 | 0.03 | 0.03 | 0.03 | 0.03 | 0.03 |
| Histidine | 0.05 | 0.10 | 0.10 | 0.10 | 0.05 | 0.10 |
| Benzyl Alcohol | 0.4 | 0.4 | 0.4 | 0.4 | 0.4 | 0.4 |
| Preservatives | 0.03 | 0.03 | 0.03 | 0.03 | 0.03 | 0.03 |

| Ingredients | Rinse-off Condition Ex. 9 | Rinse-off Condition Ex. 10 | Rinse-off Condition Ex. 11 | Rinse-off Condition Ex. 12 | Rinse-off Condition Ex. 13 | Rinse-off Condition Ex. 14 |
|---|---|---|---|---|---|---|
| Water-USP Purified & Minors | QS to 100% | QS to 100% | QS to 100% | QS to 100% | QS to 100% | QS to 100% |
| BTMS[1] | — | — | — | — | — | — |
| BTMAC[2] | 2.8 | 2.8 | 2.8 | 2.8 | 2.8 | 2.8 |
| Cetyl alcohol | 1.8 | 1.8 | 1.8 | 1.8 | 1.8 | 1.8 |
| Stearyl alcohol | 4.6 | 4.6 | 4.6 | 4.6 | 4.6 | 4.6 |
| Soy Oligomer[3] | — | — | 0.75 | — | — | — |
| Soy Oligomer Blend[4] | — | 1.0 | — | — | — | — |
| Aminosilicone[5] | 1.0 | — | 0.75 | 1.5 | 2.0 | 2.0 |
| Perfume | 0.5 | 0.5 | 0.5 | 0.5 | 0.5 | 0.5 |
| Disodium EDTA | 0.1 | 0.1 | 0.1 | 0.1 | 0.1 | 0.1 |
| Panthenol | 0.03 | 0.03 | 0.03 | 0.03 | 0.03 | 0.03 |
| Panthenyl ethyl ether | 0.03 | 0.03 | 0.03 | 0.03 | 0.03 | 0.03 |
| Histidine | 0.05 | 0.10 | 0.10 | 0.05 | 0.05 | 0.10 |
| Benzyl Alcohol | 0.4 | 0.4 | 0.4 | 0.4 | 0.4 | 0.4 |
| Preservatives | 0.03 | 0.03 | 0.03 | 0.03 | 0.03 | 0.03 |

| Ingredients | Rinse-off Condition Ex. 15 | Rinse-off Condition Ex. 16 | Rinse-off Condition Ex. 17 | Rinse-off Condition Ex. 18 |
|---|---|---|---|---|
| Water-USP Purified & Minors | QS to 100% | QS to 100% | QS to 100% | QS to 100% |
| BTMS[1] | 3.76 | 3.76 | 3.76 | 3.76 |
| BTMAC[2] | — | — | — | — |
| Cetyl alcohol | 1.3 | 1.3 | 1.3 | 1.3 |
| Stearyl alcohol | 3.2 | 3.2 | 3.2 | 3.2 |
| Soy Oligomer[3] | 1.0 | 1.0 | — | — |
| Soy Oligomer Blend[4] | — | — | — | — |
| Aminosilicone[5] | — | — | 1.0 | 1.0 |
| Perfume | 0.5 | 0.5 | 0.5 | 0.5 |
| Disodium EDTA | 0.1 | 0.1 | 0.1 | 0.1 |
| Panthenol | — | — | — | — |
| Panthenyl ethyl ether | — | — | — | — |
| Histidine | 0.10 | 0.05 | 0.05 | 0.10 |
| Benzyl Alcohol | 0.4 | 0.4 | 0.4 | 0.4 |
| Preservatives | 0.03 | 0.03 | 0.03 | 0.03 |
| Deposition Aid polymer[6] | 0.5 | — | 0.5 | — |

[1]Behenyltrimethylammonium methylsulfate, from Feixiang
[2]Behenyltrimethylammonium chloride, Genamin KDMP, from Clariant
[3]HY-3050, from Dow Corning
[4]HY-3051, from Dow Corning
[5]Y-14945; 10,000 cps aminodimethicone, from Momentive
[6]ABC1459 from Mitsubishi Chemical

Examples of Leave-on Treatment (LOT) Compositions

| Components | LOT Ex. 1 | LOT Ex. 2 | LOT Ex. 3 |
|---|---|---|---|
| Dipropyleneglycol Monomethylether | 0.500 | 0.500 | 0.500 |
| Disodium Ethylene diamine diacetic acid | 0.141 | 0.141 | 0.141 |
| PEG-40 Hydrogenated Castor Oil | 0.500 | 0.500 | 0.500 |
| Polysorbate 80[1] | 0.120 | 0.120 | — |
| Amodimethicone and Cetrimonium Chloride | 1.810 | 1.810 | 1.928 |
| Polyquaternium 11[2] | 1.335 | 1.335 | 1.335 |
| Citric Acid Anhydrous | 0.080 | 0.080 | 0.20 |
| 2-Amino-2-methyl-1-propanol | 0.100 | 0.100 | 0.100 |
| DMDM Hydantoin (55%)[3] | 0.370 | — | — |
| Benzyl Alcohol | — | 0.400 | 0.4 |
| Neolone 950 Preservative[4] | — | 0.053 | 0.053 |
| Perfume | 0.200 | 0.200 | 0.10 |

-continued

| Components | LOT Ex. 1 | LOT Ex. 2 | LOT Ex. 3 |
|---|---|---|---|
| Ethylene diamine disuccinic acid (EDDS) | 0.100 | 0.500 | |
| Water-USP Purified & Minors | QS to 100% | QS to 100% | QS to 100% |

[1]Nonionic surfactant and emulsifier derived frompolyethoxylated sorbitan and oleic acid
[2]Copolymer of vinylpyrrolidone and quaternized dimethylaminoethyl methacrylate
[3]1,3-Bis(hydroxymethyl)-5,5-dimethylimidazolidine-2,4-dione
[4]Preservative containing Methylisothiazolinone Performance Evaluation of Regimens Regimens that include (a) chelant-containing hair colorant, (b) chelant-containing hair conditioner and (c) chelant-containing shampoo products are evaluated to determine the effectiveness of such regimens to remove copper from hair. These regimens are compared to control regimens that include hair care products of the same type, but containing different chelant concentrations (or contain no chelant). It is found that certain regimens effectively remove copper form hair, protecting consumer hair against UV damage. More specifically, the following products are part of the regimen study:
(a) Oxidative dye
(b) In-box rinse-off hair conditioner;
(c) Conditioning shampoo;
(d) Daily rinse-off conditioner.

Regimen Treatment Protocol

Moderately oxidized hair switches are used for the evaluation. Each hair switch weighs 2 g and its length is 6 inches. All the hair switches used are initially exposed to copper-containing water (0.06 ppm) to a relatively constant concentration of copper among all the hair switches. After this exposure, the hair samples are taken for ICP analysis to determine copper concentration in hair.

The switches are then colored using an oxidative dyeing composition (Medium Brown), rinsed with tap water and treated with the in-box conditioner. After rinsing with tap water, the hair are resampled for determination of the copper level.

The hair switches are exposed to a 6 week wash protocol. Each week consists of the following treatments:
Day 1: Shampoo and rinse;
Day 2: Shampoo and rinse followed by rinse-off conditioner and rinse;
Day 3: Shampoo and rinse;
Day 4: Shampoo and rinse followed by rinse-off conditioner and rinse;
Day 5: Shampoo and rinse;
Day 6: Shampoo and rinse followed by in-box rinse-off conditioner and rinse;
After 3 weeks and 6 weeks (18 and 36 washes) the hair is sampled for determination of its copper concentration.

The various procedures used are provided in more detail below. For all treatments and rinsing, the water used contains 0.06 ppm of copper has Ca—Mg hardness of 7 US grains per gallon.

Method for Dosing of Hair Switches with Copper

Moderately oxidized hair switches, each weighing 2 g and having length of 6 inches, are exposed to water containing 0.06 ppm of copper and Ca—Mg hardness of 7 grains per gallon. More specifically, each switch is exposed to running water of the above mentioned specifications for 20 minutes. After this exposure, the hair samples are taken for ICP analysis (3 samples per leg) to determine copper concentration in hair.

Method of Oxidative Dyeing Followed by Hair Conditioner Treatment with In-Box Hair Conditioner The appropriate quantity of the oxidative dye composition is prepared by mixing the oxidative dye precursor+hair swelling agent part and the oxidizing agent part. The mixture is immediately applied onto the hair switch. After working the mixture a few minutes to insure uniform application to all of the hair, the oxidative dye composition is allowed to remain on the hair for 10 minutes and then rinsed with water (containing 0.06 ppm of copper) for 2 minutes. Excess water is squeezed from the hair switches and then 0.1 g/g of the in-box rinse-off conditioner is applied and milked for 30 seconds and then rinsed for 30 seconds with water containing 0.06 ppm of copper. The hair switches were dried in a heat box (60° C.) until dry.

Shampoo Treatment Method

Each wash cycle consists of two applications of 0.1 g/g of shampoo to the hair switches. Each application consists of adding shampoo to the hair, milking for 30 seconds followed by rinsing for 30 secs with water (containing 0.06 ppm of copper). Shampoo is then reapplied 0.1 g/g, milked for 30 seconds, rinsed for 30 seconds with water (containing 0.06 ppm of copper) and then dried in a heat box (60° C.) until dry.

Shampoo Treatment Followed by Hair Conditioner Treatment Method

Each wash cycle consists of two applications of 0.1 g/g of shampoo to the hair switches. Each application consists of adding shampoo to the hair, milking for 30 seconds followed by rinsing with water (containing 0.06 ppm of copper) for 30 secs. Shampoo is then reapplied 0.1 g/g, milked for 30 secs, rinsed with water (containing 0.06 ppm of copper) for 30 seconds. Excess water is squeezed from the hair switches and then 0.1 g/g of a rinse-off conditioner is applied and milked for 30 seconds and then rinsed with water (containing 0.06 ppm of copper) for 30 seconds. The hair switches were dried in a heat box (60° C.) until dry.

Method of Determination of Copper Concentration of Hair

Samples of 100 mg of hair are digested overnight with 2 ml of high purity concentrated nitric acid. The digestive mixture also contains 150 μL of 100 μg/g Yttrium internal standard (Inorganic Ventures, Christianburg, Va., USA). Following digestion, samples are heated to 70-80° C. for one hour, cooled to room temperature and diluted to 15 mL with deionized water. Copper content of the hair switches are determined by inductively coupled plasma atomic spectroscopy (ICP-OES). For each leg, 3 different samples are analyzed.

The table below summarizes the compositions that are used and the evaluation results that are obtained for the complete protocol in terms of the ability of each set of compositions to remove copper from hair.

The following Table provides the product sets that are evaluated according to the regimen described under the section REGIMEN TREATMENT PROTOCOL. The Table also provides the results of the determination of the concentration of copper in the hair.

|  | Hair Colorant | Shampoo | Daily Rinse-off (First) Conditioner | In-Box (second) Rinse-off Conditioner | Hair Copper Content | | | |
|---|---|---|---|---|---|---|---|---|
|  |  |  |  |  | After Initial Dosing (ppm) | After Coloring (ppm) | After 3-Week Treatment (ppm) | After 6-Week Treatment (ppm) |
| Leg A | Colorant Ex 1 (contains 0.1% EDDS) | Shampoo Ex 1 | Rinse-off Conditioner Ex 1 | In-Box Conditioner Ex 1 | 28.6 | 19.3 | 50.3 | 61.6 |
| Leg B | Colorant Ex 1 (contains 0.1% EDDS) | Shampoo Ex 1 | Rinse-off Conditioner Ex 1 | In-Box Conditioner Ex 2 (contains 0.1% histidine) | 31.8 | 17.5 | 39.3 | 51.4 |
| Leg C | Colorant Ex 1 (contains 0.1% EDDS) | Shampoo Ex 1 | Rinse-off Conditioner Ex 1 | In-Box Conditioner Ex 3 (contains 0.25% histidine) | 32.2 | 16.6 | 36.2 | 46.4 |
| Leg D | Colorant Ex 1 (contains 0.1% EDDS) | Shampoo Ex 2 (contains 0.1% EDDS) | Rinse-off Conditioner Ex 2 (contains 0.05% histidine) | In-Box Conditioner Ex 3 (contains 0.25% histidine) | 28.9 | 16.0 | 29.8 | 33 |
| Leg E | Comparative Product from the market (Medium Brown) | Comparative shampoo product from the market (for colored hair) | Comparative rinse-off conditioner product from the market (for colored hair) | Comparative in-box conditioner product from the market | 37.0 | 29.9 | 61.4 | 74.5 |

To note, there is some variation in the starting copper levels of hair switches after the dosing even though the differences are not significant. This is expected due to the inherent variability of this dosing method.

The results included in FIG. 1 indicate that the addition of a chelant into the in-box (second) conditioner provides a significant copper removal benefit (Leg B versus Control Regimen A) and taking into account that hair samples form Regimens A, B, C and D contain similar concentration of copper before the in-box (second) conditioner application. With more benefit observed at the higher histidine content as concluded by comparison of Regimen C and Regimen B (C more effective than B). Additional copper can be removed from hair if chelant is added into the shampoo and daily rinse-off (first) conditioner (Regimen D is more effective than Regimen C). Thus, the evaluation data supports the incremental benefit of using chelants throughout the regimen to reduce copper. The regimens described herein perform better than Comparative Product regimen in reducing copper content of hair.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of inhibiting copper deposition on hair on hair comprising the steps of
   (a) applying to the hair a hair colorant composition selected from the group consisting of bleaching compositions and an oxidative dyeing compositions comprising about 0.025% to about 1% ethylenediamine-N,N'-disuccinic acid;
   (b) rinsing said hair colorant composition from the hair with water;
   (c) applying to the hair a first conditioner composition comprising:
      (1) from about 0.025% to about 0.25% histidine, by weight of the conditioner composition;
      (2) a conditioner gel matrix comprising (i) from 0.1% to about 20% of one or more high melting point fatty compound, by weight of the conditioner gel matrix;
(ii) from about 0.1% to about 10% of a cationic surfactant system, by weight of the conditioner gel matrix; and
(iii) at least 20% of a second aqueous carrier, by weight of the conditioner gel matrix;
(3) from about 1% to about 8% of a silicone;
(d) rinsing said conditioner first composition from the hair with water;
(e) applying to the hair a shampoo composition, having a pH of from about 2 to about 7 and comprising
(1) from about 0.05% to about 1% of a compound selected from the group consisting of ethylenediamine-N,N'-disuccinic acid, derivatives of ethylenediamine-N,N'-disuccinic acid, salts of ethylenediamine-N,N'-disuccinic acid, salts of derivatives of ethylenediamine-N,N'-disuccinic acid and mixtures thereof, by weight of the shampoo composition; and
(2) from about 2% to about 50% of one or more detersive surfactants, by weight of the shampoo composition;
(f) rinsing said shampoo composition from the hair with water;
(g) applying to the hair a second conditioner composition comprising
(1) from about 0.025% to about 0.25% histidine, by weight of the second conditioner composition;
(2) a conditioner gel matrix comprising
(i) from 0.1% to about 20% of one or more high melting point fatty compound, by weight of the conditioner gel matrix;
(ii) from about 0.1% to about 10% of a cationic surfactant system, by weight of the conditioner gel matrix; and
(iii) at least 20?/o of a second aqueous carrier, by weight of the conditioner gel matrix;
(h) rinsing said second conditioner composition from the hair with water;
wherein steps (e), (f), (g), (h) are repeated one or more times until the desirable hair copper content is achieved; and
(i) a leave-on treatment comprising 0.05-0.5% of a rheology modifier and about 0.025% to about 1%, by weight of a chelating compound selected from the group consisting of ethylenediamine-N,N'-disuccinic acid (EDDS), derivatives of ethylenediamine-N,N'-disuccinic acid, salts of ethylenediamine-N,N'-disuccinic acid, salts of derivatives of ethylenediamine-N,N'-disuccinic acid, histidine and mixtures thereof, the leave-on treatment applied after any of steps (d) (f) or (h).

2. The method of claim 1, wherein the method mitigates the absorption of copper in hair to an increase of less than 20%, measured by the increased copper content after the completion of steps (a) to (h) and repetition of steps (e), (f), (g), (h) twenty times, using water containing 0.06 ppm of copper from the copper content before the application of the method.

3. The method of claim 1, wherein the method mitigates the absorption of copper in hair to an increase of less than 10%, measured by the increased copper content after the completion of steps (a) to (h) and repetition of steps (e), (f), (g), (h) twenty times, using water containing 0.06 ppm of copper from the copper content before the application of the method.

4. The method of claim 1, wherein the bleaching composition or the oxidative dyeing composition comprises from about 0.01% to about 0.25% a compound selected from the group consisting of ethylenediamine-N,N'-disuccinic acid, derivatives of ethylenediamine-N,N'-di succinic acid, salts of ethylenediamine-N,N'-disuccinic acid, salts of derivatives of ethylenediamine-N,N'-disuccinic acid, histidine and mixtures thereof, by weight of the bleaching or the oxidative dyeing composition.

5. The method of claim 1, wherein step (h) is followed by a repetition of steps (c) and (d) or steps (g) and (h) one time.

6. The method of claim 1, wherein step (h) is followed by a repetition of steps (c) and (d) or steps (g) and (h) more than one time.

7. The method of claim 1, wherein the first conditioner composition comprises from about 3% to about 8% of silicone by weight of the first conditioner composition.

8. The method of claim 1, wherein the first conditioner compositions comprises from about 0.05% to about 0.2% histidine by weight of the first conditioner composition.

9. The method of claim 1, wherein the second conditioner composition comprises from about 0.05% to about 0.2% histidine by weight of the second conditioner composition.

10. The method of claim 1, wherein the shampoo, the first conditioner composition and/or the second conditioning composition further comprises one or more additional benefit agents, wherein the one or more additional benefit agents is selected from the group consisting of conditioning agents, anti-dandruff agents, vitamins, chelants, perfumes, brighteners, enzymes, sensates, attractants, anti-bacterial agents, dyes, pigments, bleaches, and mixtures thereof.

11. The method of claim 1, wherein the one or more additional benefit agents is a conditioning agent, wherein the one or more additional benefit agents is a silicone.

12. The method of claim 1, wherein the silicone is selected from the group consisting of amodimethicone, a silicone resin, a dimethicone, a dimethiconol, and mixture thereof.

13. The method of claim 1, wherein the first conditioner composition further comprises from about 2% to about 8% silicone by weight of the first conditioner composition, wherein the silicone is selected from the group consisting of amodimethicone, a silicone resin, a dimethicone, a dimethiconol, and mixture thereof.

14. The method of claim 1, wherein the second conditioner composition further comprises from about 4% to about 6% silicone by weight of the second conditioner composition, wherein the silicone is selected from the group consisting of amodimethicone, a silicone resin, a dimethicone, a dimethiconol, and mixture thereof.

15. The method of claim 1, wherein the shampoo composition comprises from about 0.05% to about 0.2% of a compound selected from the group consisting of ethylenediamine-N,N'-disuccinic acid, derivatives of ethylenediamine-N,N'-disuccinic acid, salts of ethylenediamine-N,N'-di succinic acid, salts of derivatives of ethylenediamine-N,N'-disuccinic acid, histidine, and mixtures thereof, by weight of the shampoo composition.

16. The method of claim 15, wherein the shampoo composition comprises from about 0.1% to about 0.15% of a compound selected from the group consisting of ethylenediamine-N,N'-disuccinic acid, derivatives of ethylenediamine-N,N'-disuccinic acid, salts of ethylenediamine-N,N'-disuccinic acid, histidine, and mixtures thereof, by weight of the shampoo composition.

17. The method of claim 16, wherein the compound is histidine.

18. The method of claim 1, wherein the shampoo composition has a pH of from about 3 to about 4.25.

19. The method of claim 18, wherein the shampoo composition has a pH of about 4.25.

* * * * *